United States Patent
Herrmann et al.

(10) Patent No.: US 6,922,061 B2
(45) Date of Patent: Jul. 26, 2005

(54) METHOD OF DETECTING FOREIGN BODIES IN MASS STREAMS

(75) Inventors: Rainer Herrmann, Hamburg (DE); Stefan Zaage, Hannover (DE); Harald Ceslik, Hamburg (DE)

(73) Assignee: TEWS Elektronik, Dipl. ing. Manfred Tews, Hamburg (DE)

( * ) Notice: Subject to any disclaimer, the term of this patent is extended or adjusted under 35 U.S.C. 154(b) by 17 days.

(21) Appl. No.: 10/340,453

(22) Filed: Jan. 9, 2003

(65) Prior Publication Data

US 2003/0141880 A1 Jul. 31, 2003

(30) Foreign Application Priority Data

Jan. 11, 2002 (EP) ............................................ 02000725

(51) Int. Cl.$^7$ .............................................. G01R 27/32
(52) U.S. Cl. ...................... 324/633; 324/634; 324/636; 324/640
(58) Field of Search ................................ 324/633, 634, 324/636–640; 131/286

(56) References Cited

U.S. PATENT DOCUMENTS

| | | | | |
|---|---|---|---|---|
| 5,016,653 A | * | 5/1991 | Lassiter ...................... | 131/286 |
| 5,397,993 A | * | 3/1995 | Tews et al. .................. | 324/634 |
| 2002/0121906 A1 | * | 9/2002 | Moller et al. ............... | 324/639 |

FOREIGN PATENT DOCUMENTS

| | | |
|---|---|---|
| EP | 0 889 321 A1 | 1/1999 |
| JP | 63045547 | 2/1988 |
| JP | 63210757 | 9/1988 |
| WO | WO 02/09539 A1 | 2/2002 |

OTHER PUBLICATIONS

European Search Report EP 02000725, dated Aug. 6, 2002.

Thomas Boltze, "A Microwave Model For Moisture Determination In Bulk Materials And A Maximum Likelihood Estimation Algorithm", TH1B–6, 1995 IEEE MTT–S Digest.

* cited by examiner

Primary Examiner—N. Le
Assistant Examiner—Timothy J. Dole
(74) Attorney, Agent, or Firm—Alix, Yale & Ristas, LLP

(57) ABSTRACT

The method of detecting foreign bodies in continuous mass streams of fibrous material, strand-like material or material similar to bulk goods with the aid of microwaves, in which the mass flow is led through the field of a microwave resonator and in which the change (A) in the resonant frequency, effected by the material, and the change (B) in the width of the resonance curve of the microwave resonator is determined, is distinguished in that the ratio (B/A) of the changes is evaluated and compared with corresponding averages, and the presence of a foreign body is reported when the ratio differs from the averages by more than a predefined value.

7 Claims, No Drawings

METHOD OF DETECTING FOREIGN BODIES IN MASS STREAMS

BACKGROUND OF THE INVENTION

The invention relates to a method of detecting foreign bodies in continuous mass streams of fibrous material, strand-like material or material similar to bulk goods with the aid of microwaves, in which the mass flow is led through the field of a microwave resonator and in which the change (A) in the resonant frequency, effected by the material, and the change (B) in the width of the resonance curve of the microwave resonator is determined.

In numerous processes in the processing industry, in which nonmetallic products are processed in mass streams, foreign bodies which have unintentionally got into the product stream normally have an extremely damaging effect on the following process steps, the quality of the product or the production plant.

For example, during the production of yarns in the textile industry, good homogeneity in the preparation for spinning is already important if the cotton and plastic fibers are aligned in parallel and homogenized in carding and drawing devices. Inhomogeneities in the fiber distribution, caused by incorporated foreign bodies or neps, have an effect in the final product, the finished woven material or the curtain, as a reduction in quality which is obvious to any customer. It is therefore a matter of outputting a warning in good time, by measuring with the aid of microwave resonators, as early as in the spinning preparation machine and, if appropriate, of arranging for the foreign body to be removed manually or automatically.

In the production of cigarettes, the bales of tobacco supplied from the tobacco growing regions are sometimes contaminated with all kinds of foreign bodies, such as textile residues, pieces of plastic, rubber parts, metal wires, timber residues or insects. In addition, on the long paths from tobacco preparation to the cigarette machine, foreign bodies can get into the tobacco as a result of inattention. Ultimately, a foreign body which has not been eliminated from a cigarette not only means an extreme reduction in the quality of the cigarette but, depending on the type of the foreign body during the combustion and inhalation of the smoke, a hazard to the consumer if a halogen acid can be produced, such as during the combustion of halohydrocarbons. It is therefore a matter, by means of reliable detection of foreign bodies at a point where foreign bodies can no longer get into the tobacco (for example during the formation of the cigarette rod and wrapping it with paper) with the aid of a microwave resonator after the rod has been cut up into pieces of rod, of arranging for the contaminated cigarette to be removed automatically. Since these removed cigarettes can no longer be recycled but are burned, a high requirement is placed on the measurement technique, for economic reasons: the erroneous rejection rate with still reliable foreign body detection may not exceed one per thousand of the cigarettes produced since, even at this rate, in the case of about 200 billion cigarettes typically produced per company per year, 200 million would be destroyed as contaminated.

In many branches of the chemical industry, undesired foreign bodies can lead not only to a reduction in the product quality but also to damage to the production plants. Cellulose acetate synthetic fibers (mainly used for the production of cigarette filters) are produced from cellulose acetate granules dissolved in acetone by being pressed out of fine spinning nozzles.

Foreign bodies in the granules, which do not go into solution, can block up the spinning nozzles and lead to fiber breakages during the fiber production. Glass is produced from molten quartz sand. Foreign bodies in the quartz sand can lead to irreparable damage to the melting furnaces. Here, too, it is a matter, by means of the product management of the bulk material by means of a suitable measuring arrangement, of detecting the changed material composition owing to a foreign body and of arranging for the latter to be removed without the enormous density fluctuations, which occur at the same time in the pouring process having a detrimental effect on the measurement.

Foreign bodies are therefore to be understood firstly to mean all critical changes in the physical or chemical composition of a product which go beyond the normal statistical fluctuation of the composition of the product stream around a typical average at the measurement point. This also includes metallic contaminants. Secondly, however, in the case of a constant composition, this can also be understood to mean large mass flow fluctuations, for example extreme density minima as a result of voids in the cigarette or maxima as a result of excessive proportions of ribs or material thickenings in the textile strand being formed.

Detection methods for individual specific types of foreign bodies have been known for a long time, such as inductive metal detectors (e.g. DE 3714009 A1, Schroder, Hauni, Hamburg 1987). However, these only act on a specific type of foreign bodies, have an effect which is only severely restricted and on most foreign bodies no effect at all.

More general foreign body detection methods have primarily been disclosed in the tobacco industry in the last decade. Attempts have been made to utilize the changed flow behavior of some foreign bodies to remove them by means of specific air swirling (e.g. U.S. Pat. No. 5,267,576 Heitmann, Hauni, Hamburg 1992) or (WO 00/40105, Rizzolo, Fabriques de Tabac Reunies, Neuchatel, 1998). In this case, however, the only limited efficiency of these plants has been shown in practice. A specific proportion of primarily coarse foreign bodies is certainly removed as a function of its geometric shape, but the generally finely cut, fibrous foreign bodies are not registered.

Many attempts have been made to detect foreign bodies with the aid of optical detectors, preferably infrared detectors, and to eliminate them by blowing them out with air. (U.S. Pat. No. 4,657,144, Martin, Philip Morris, New York, 1985) or (U.S. Pat. No. 5,476,108, Dominguez, R. J. Reynolds Tobacco Company, Winston Salem, 1992). Since optical or IR sensors can barely penetrate the surface of the product being investigated, however, the product must be spread out to form a very thin layer in order to achieve optical detection of the foreign bodies (DE 4325838, Roether, Hauni, Hamburg, 1993). For this reason, these methods can also be used only at the positions where such spreading out of the material flow is possible, that is to say for example not on the finished tobacco rod covered with paper. In this case, however, similarities in the surface and color between foreign body and product stream lead to many foreign bodies not being detected. In addition, spreading out the main stream of the product to be examined at the high throughput rates which are generally normal in industrial processes leads to swirling of the product, so that an optically detected foreign body also changes its position because of the swirling and cannot be blown out.

It is known to evaluate microwaves of very short wavelength (5 to 3 mm, that is to say at frequencies from 40 to 90 GHz), whose wavelength must lie in the range of the physical extent of the foreign bodies to be detected, with regard to their scattering behavior on foreign bodies and to use them for foreign body detection (U.S. Pat. No. 4,707, 652, Lowitz, Philip Morris Inc., New York, 1985). Since the penetration of electromagnetic waves into a dielectric product is approximately of the order of the wavelength, owing to the microwave attenuation resulting from the material moisture, the behavior has only a limited effect, owing to the limited penetration depth. Furthermore, in particular not just foreign bodies act as scattering centers but also all density fluctuations in the normal product stream, such as cannot be avoided at all in typical fibrous material or bulk goods.

A transillumination method is also known, in which the product is located between a transmitting and a receiving antenna, with which foreign bodies are to be detected (WO 00/09983, Moshe, Malcam Ltd. Nazareth-Israel, 1998). However, this method has the disadvantage that, as is also the case in other transillumination methods, the received signal also depends very critically on other changes in the material stream. The method is therefore inaccurate and requires very complicated evaluation using neural networks or "fuzzy logic" (pp. 32/33 of the citation).

In a proposed method of the type mentioned at the beginning (WO 02/09539 A1), combination signals on the basis of the changes in the resonant frequency and the width of the resonance curve are calculated in order to detect foreign bodies.

SUMMARY OF THE INVENTION

Briefly stated, the invention in a preferred form is a method of detecting foreign bodies in continuous mass streams of fibrous material, strand-like material or material similar to bulk goods. The mass flow is led through a field of a microwave resonator resulting in a change (A) in the resonant frequency and a change (B) in the width of the resonance curve of the microwave resonator. The ratio (B/A) of the changes is evaluated and compared with corresponding averages, and the presence of a foreign body is reported when the ratio differs from the averages by more than a predefined value.

The object of the invention consists in providing a simple and reliable method of detecting the foreign bodies.

Other objects and advantages of the invention will become apparent from the specification.

DETAILED DESCRIPTION OF THE PREFERRED EMBODIMENT

The solution according to the invention consists in the ratio (B/A) of the changes being evaluated and compared with corresponding averages and the presence of a foreign body being reported when the ratio differs from the averages by more than a predefined value.

At the resonant frequency, microwave resonators form a standing wave through which, with the aid of special openings and product guides lined with dielectric material, the material to be measured, including the foreign bodies to be detected, is moved. By means of the specific interaction between the standing microwave and the product, the resonant properties of the microwave resonator are changed. The main advantages of these resonators are that, by means of geometrical configuration, they can be adapted to an extremely wide range of applications, that in spite of relatively long wavelengths of up to 30 cm, a high-resolution zone of the interaction with the product down to 1 mm can be achieved by means of field focusing and, at the same time, nevertheless a great penetration depth into the product can be achieved. In addition, as opposed to transillumination measurement techniques, the measurement of the losses of microwave energy arising from the absorption into the product exhibits the quality of an exact measured variable which, in the case of transillumination measurements, is not provided, because of the scattering losses which cannot be registered.

Exemplary embodiments of such resonators to achieve a high local resolution down to 1 mm are the profile sensor which, with sample tube diameters of 5–20 mm, can be used for example in the tobacco rod of a cigarette or cigar machine (EP 0 889 321 A1, Herrmann, Tews, 1998). For a sideways measurement of flat product such as paper webs, films or thin layers, the planar sensor is suitable, having a standing wave over a planar surface, whose scattered field decreases exponentially, starting from the sensor surface, down to an extent of 10 cm in space (EP 0 908 718 A1, Herrmann et al., Tews, 1998). For bulk goods or relatively wide pieces of textile fiber, a sensor type whose microwave measurement field can be built up very homogeneously in a measuring gap which is up to 3 cm wide and 30 cm long is particularly suitable, so that for the intensity of the interaction between microwave and product, the position of the product in the sensor is unimportant. This "fork resonator" is a resonator which is excited in the basic EO10 mode and which is chopped in the direction of the wall streams, so that the result is a measurement zone with an extremely homogeneous measuring field (EP 0 468 023 B1, Tews et al., Tews, 1991).

In the case of the microwave resonator measuring technique, two variables arise as direct measured variables: the change A in the resonant frequency and the change B in the width of the resonance curve as compared with the empty state of the resonator. The first effect of the resonant frequency detuning A depends primarily on the shortening of the wavelength via the dielectric product which is currently located in the measuring field of the resonator (that is to say on the so-called real part of the dielectric constant). The second effect B is brought about by the conversion of the microwave energy into heat, which can be measured exactly only in the resonator method (the "microwave oven effect" or the so-called imaginary part of the dielectric constant). The measuring technique developed by the applicant has been optimized to the achievement of a high measuring speed and precision in such a way that, in each case after 0.1 milliseconds, a new A and B value can be output, that is to say 10,000 A values and 10,000 B values per second.

According to the invention, it has now been found that, by evaluating the change A in the resonant frequency and the change B in the width of the resonance curve, foreign bodies in the mass flow can be detected simply and reliably by the continuously measured values being compared with averages and, in the event of a deviation which goes beyond a predetermined extent, a foreign body being reported. This report can trigger an acoustic or optical warning signal or, advantageously with a suitable device, can effect the removal of the relevant part of the material flow.

The methods by which these two measured variables A and B are determined is of secondary importance for the invention. The microwave frequency is normally varied in such a way that the instantaneous resonance curve is passed through and, as a result, the maximum, the resonant frequency, and the half-value width are determined. The comparison with the stored data for the empty resonator then supplies the basic measured variables A and B. However, by means of controlled tracking of the resonance curve, it is possible to achieve the situation where the measuring instrument always operates the resonator at resonance and draws conclusions about the half-value width from the decrease in the resonant amplitude as compared with that of the empty state. Alternatively, two or more fixed frequencies are used and the behavior of the resonance with and without product is observed in order to get to the variables A and B. Even in the case of a single frequency, which can be swept slightly, it is possible to use the current signal from the part of the observed resonance curve and its slope to draw conclusions about the resonant frequency which currently applies and the width or half-value width of the resonance curve.

To detect the foreign bodies in the observed product stream, it is important that both direct measured variables A and B depend on three factors:

$$A = F * K_A * M$$

$$B = F * K_B * M$$

1. The Field Factor F:

Both variables A and B depend in the same way on the intensity of the microwave measuring field which is formed at the location of the sample. In the simplest case, this factor can be specified as the ratio between the electric field energy in the physical region of the sample and that in the entire resonator.

2. The Mass M:

Both variables depend in the same way on the mass M of the product which is currently located in the field. This simple linear relationship has hitherto proven to be valid in all cases in practical testing. In principle, more complex relationships could be represented by a series expansion in M with a vanishing absolute element. In fact, the series can be terminated after the first element with satisfactory accuracy. This expresses the fact that, with a constant material mixture both the differences in the real part and those in the imaginary part of the dielectric constant are variables exhibiting mass proportionality with respect to vacuum.

3. The Concentration Factors $K_A$ and $K_B$:

These express which proportion the different material components possess in making up the two variables A and B. Because of the different nature of the physical processes on which the variables A and B are based, these two constants are also different in terms of the weighting of the components of a material mixture. For example, a foreign body in the form of a plastic part can have a large proportion relating to the resonant frequency detuning A, but virtually no proportion relating to the heat losses B of the microwave energy. If the concentration variable of the foreign body in the product part which is currently located in the measuring field is $C_{FK}$, and $C_H$ is the concentration of the product stream which is currently located in the measuring field, then the following is true of the variables $K_A$ and $K_B$, corresponding to the relative proportions of the dielectric constants of the components of the mixture:

$$K_A = E'_H * C_H + E'_{FK} * C_{FK}$$

$$K_B = E''_H * C_H + E''_{FK} * C_{FK}$$

$$C_H = M_H / M$$

$$C_{FK} = M_{FK} / M$$

However, it therefore becomes clear that the ratio between the two direct microwave measured variables B and A remains constant as long as nothing changes in the material composition. Mass fluctuations in the product stream (for example in the case of bulk goods or in the tobacco rod) certainly have an influence on B as on A, but not on the ratio between the two variables. On the other hand, if there is a change in the composition of the product which is currently located in the measuring field of the resonator, for example because of the presence of a foreign body, then the ratio B/A also changes.

Given an otherwise constant composition of the material in the product stream, the detection of foreign bodies therefore consists in the measuring instrument dividing the two measured variables B and A by each other carrying out sliding averaging and comparing each current B/A value with the sliding average. If the individual value of B/A differs from the sliding average beyond an adjustable minimum amount, then the foreign body is deemed to be detected and an alarm message or electro mechanical arrangement for ejection can be activated.

As a rule, however, the homogeneity of the composition of the product stream is not ideal either but characterized by statistical fluctuations. This arises, for example, as a result of fluctuations in the moisture content of the material, which corresponds to a continual change in the composition of the material. The statistical fluctuation of the value of B/A about an average, occurring as a result, then also requires the separation of the change in B/A as a result of statistical material fluctuations and that as a result of a foreign body. In this case, too, the deviation of the individual value with respect to the sliding average which exceeds the normal statistical fluctuation is a measure of the presence of a foreign body: the adjustable threshold for the detection must be matched to the normal statistical fluctuation.

However, for fluctuations of B/A which lie within the statistical fluctuation range of the product stream, the resonator method can also be used to detect foreign bodies. To this end, the effect of a foreign body on the expression B/A can be compared with the effect on the mass-proportional variable A: for instance, if a minimum in the time variation of B/A also occurs within the normal statistical fluctuation, typically as a result of the rapid movement of a foreign body through the measuring field, and if this coincides with the simultaneous occurrence of a maximum in the time variation of A, then it is possible with great probability to assume the presence of a foreign body. This is the case with foreign bodies in the form of plastics, rubber parts, etc., which barely effect any change in B but certainly effect an increase in A, corresponding to the relative proportions of the real and imaginary part of the foreign body in relation to that of the product stream. However, there are also foreign bodies in which a local maximum of B/A coincides with a maximum of A (e.g. wet pieces of wood in tobacco) or a local maximum of B/A coincides with a minimum of A (e.g. light foreign body parts of low density and higher moisture in the main stream of high density and low moisture). Critical for the detection is the chronological coincidence of the movement in the concentration expression B/A and in A. For this purpose, the calculation of chronologically closely limited correlation coefficients are a good aid.

Under certain circumstances, however, the sole interrogation of the variable A also makes sense for foreign body detection if, for example, only a material void in the tobacco rod or material compaction in textile fibers is to be detected and screened out. A fault of this type is then deemed to be detected when the individual value has moved away from the sliding average by an adjustable minimum threshold.

In summary, it can be recorded that both microwave resonator measured variables B/A and A are suitable for foreign body detection. On the one hand, they can each be evaluated on their own: B/A is suitable in the case of sufficiently large foreign bodies which change the composition of the material to a considerably greater extent than is given by the normal statistical fluctuations. A is suitable for the detection of extreme mass fluctuations, such as occur in holes or compactions. In both cases, the deviation of the individual microwave foreign body value B/A or A is compared with the sliding average of B/A or A and, if an adjustable threshold is exceeded, is indicated as a foreign body signal. In the other case, if the foreign body signals are not so pronounced, the chronological coincidence of extreme values of B/A and those of A, and the establishment of a close correlation between the two signals supplies a reliable pointer to a foreign body. Distinguishing between the various cases can be carried out automatically during the measurement.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A method of detecting foreign bodies in continuous mass flow of fibrous material, strand-like material or material similar to bulk goods comprising the steps of:

leading the mass flow through a field of a microwave resonator emitting microwaves having a known resonant frequency and a known resonance curve width;

determining a change (A) in the resonant frequency and a change (B) in the width of the resonance curve of the microwave resonator effected by the mass flow;

comparing a ratio (B/A) of the changes with corresponding averages; and reporting the presence of a foreign body when the ratio differs from the corresponding averages by more than a predefined value.

2. The method of claim 1, wherein the corresponding averages are sliding averages.

3. The method of claim 2, further comprising the step of providing a warning signal if a foreign body is detected.

4. The method of claim 2, further comprising the step of removing a part of the mass flow containing the foreign body when a foreign body is detected.

5. The method of claim 1, further comprising the step of providing a warning signal if a foreign body is detected.

6. The method of claim 5, further comprising the step of removing a part of the mass flow containing the foreign body when a foreign body is detected.

7. The method of claim 1, further comprising the step of removing a part of the mass flow containing the foreign body when a foreign body is detected.

* * * * *